United States Patent [19]

Muller

[11] Patent Number: 4,753,249

[45] Date of Patent: Jun. 28, 1988

[54] URINOMETER AND PATIENT RECORD COMBINATION

[75] Inventor: Louis F. Muller, El Segundo, Calif.

[73] Assignee: Davstar Industries, Inc., Newport Beach, Calif.

[21] Appl. No.: 15,112

[22] Filed: Feb. 17, 1987

Related U.S. Application Data

[63] Continuation of Ser. No. 632,181, Jul. 19, 1984, abandoned.

[51] Int. Cl.⁴ .............................................. H61B 5/00
[52] U.S. Cl. .................................... 128/771; 128/760
[58] Field of Search ............... 128/760, 761, 762, 771; 73/204, 219, 290 R, 292, 294, 295

[56] References Cited

U.S. PATENT DOCUMENTS

| | | | |
|---|---|---|---|
| 3,620,676 | 11/1971 | Davis | 128/771 |
| 4,187,722 | 2/1980 | Layton | 128/771 X |
| 4,305,405 | 12/1981 | Meisch | 128/762 |
| 4,384,485 | 5/1983 | Layton et al. | 73/215 |
| 4,448,207 | 5/1984 | Parrish | 73/290 R |

Primary Examiner—Edward M. Coven
Attorney, Agent, or Firm—Henry M. Bissell

[57] ABSTRACT

A urinometer which prints out a patient record corresponding to the flow rate measurement. One embodiment of the invention comprises a Drake urinometer unit which is modified to generate the patient record automatically. Other embodiments of the invention include components which are fabricated by a vacuum forming process to provide low cost units which are disposable after a single use. One of these embodiments prints out a patient record on photosensitive paper. Another embodiment prints out a patient record on blotting paper. Another embodiment of the invention incorporates a specimen collector and a coupling arrangement whereby the urinometer automatically discards the initially voided urine so that a mid-stream (clean catch) sample can be collected automatically.

36 Claims, 3 Drawing Sheets

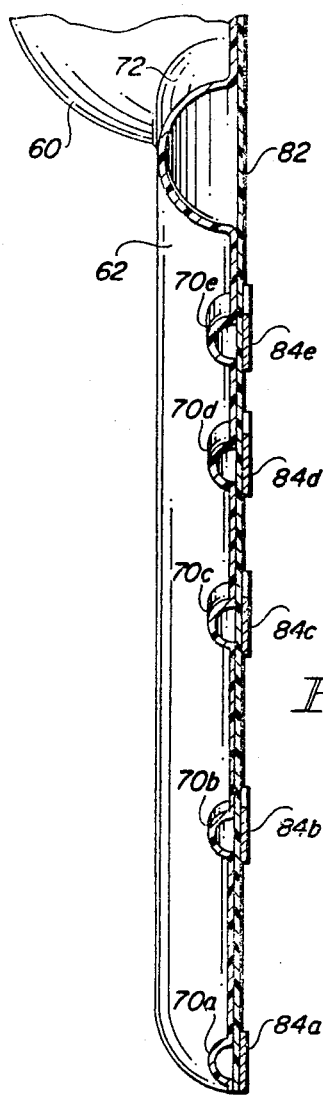
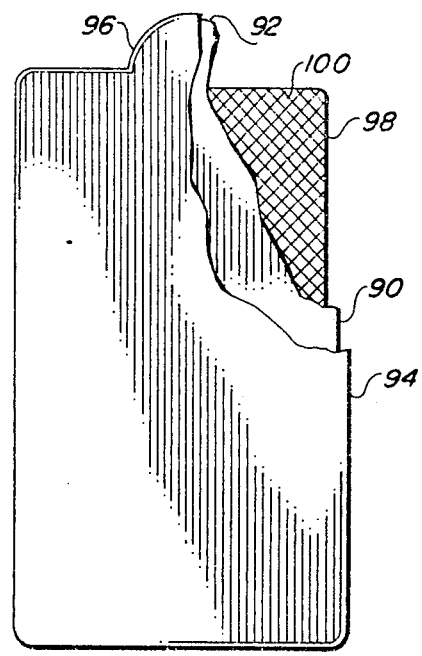
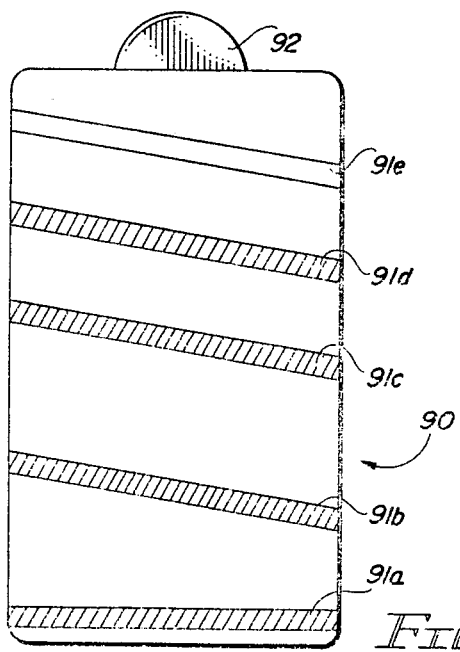
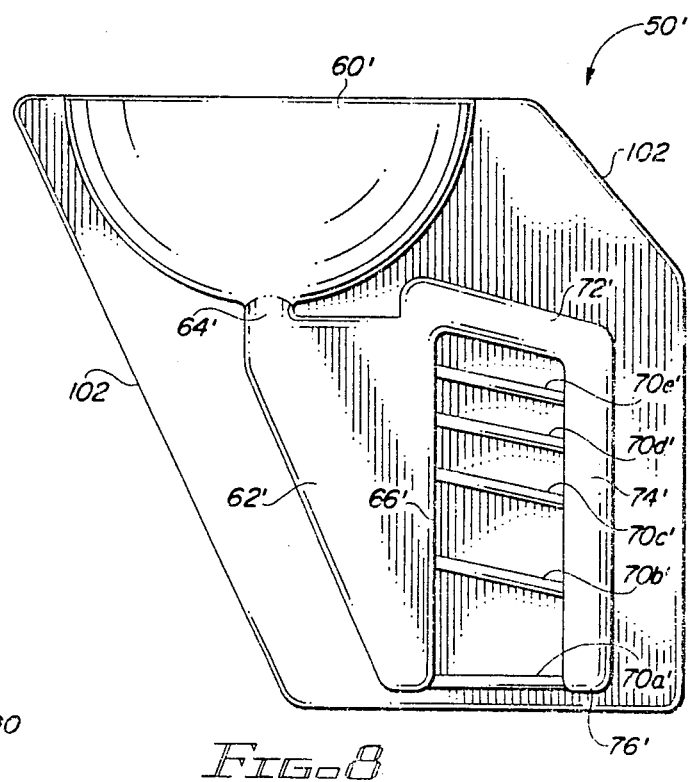

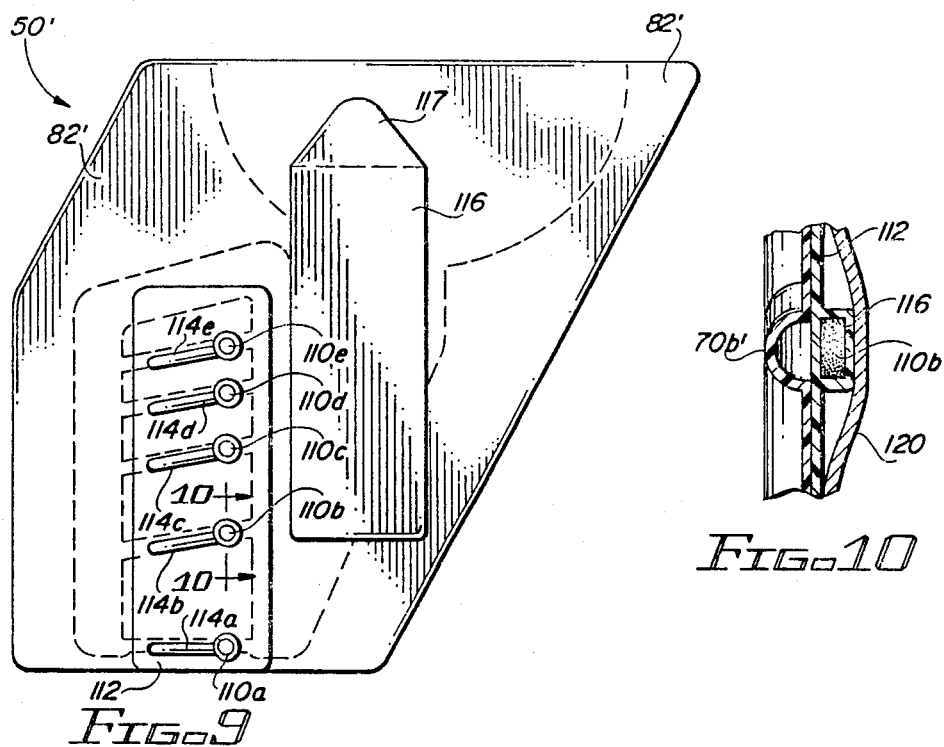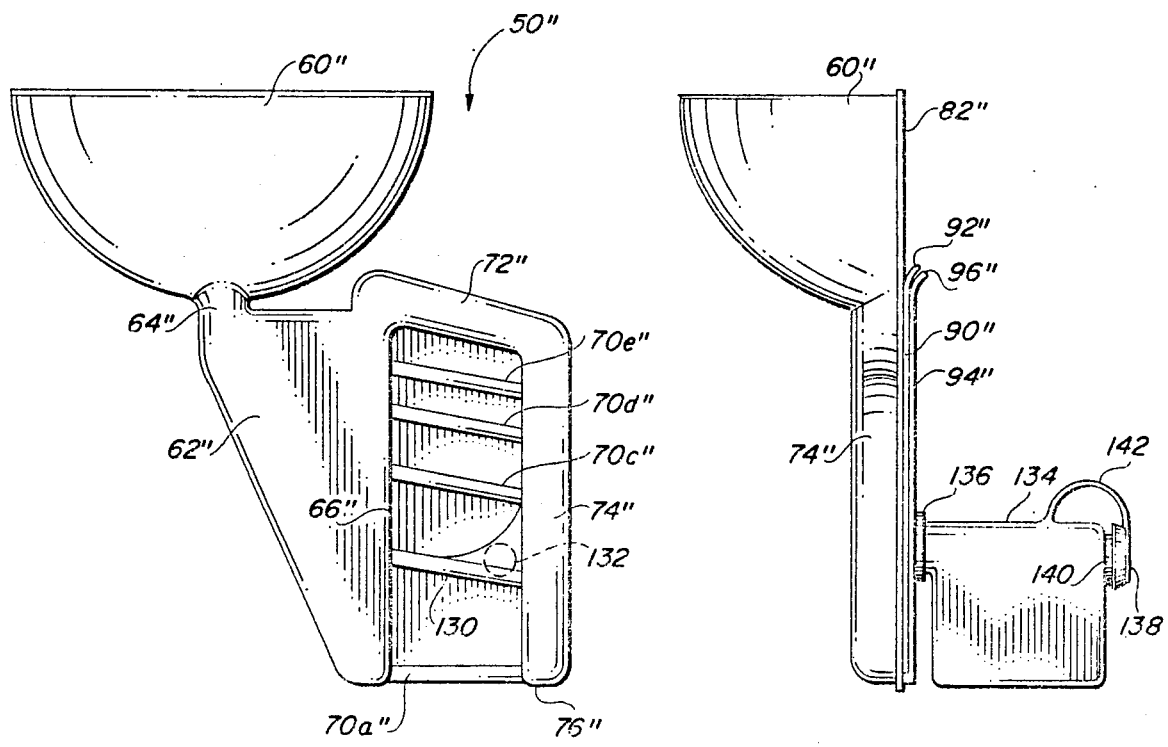

URINOMETER AND PATIENT RECORD COMBINATION

This is a continuation of application Ser. No. 632,181, filed July 19, 1984, abandoned.

BACKGROUND OF THE INVENTION

1. Field of the Invention.

This invention relates to urinometers and, more particularly, to such devices for performing a flow rate measurement and automatically printing out a patient record thereof.

2. Description of the Prior Art

In the field of urology, it is often desirable for proper diagnosis and treatment of certain pathological conditions to have a reasonably accurate indication of the rate at which a patient is able to pass urine. One obvious way of determining this measurement, of course, is to have an observer with a stop watch who records the time taken to void a measured amount of urine. One problem with this direct approach, however, is that the administration of this method creates embarrassment or psychological difficulties for many patients to the extent that normal voiding is inhibited. Thus, if the patient voids at all under such conditions, the potentially erroneous data obtained may result in a false diagnosis and a loss of confidence in the results obtained by the physician. Many devices which have been developed in the past for the collection of urine for use in diagnosis of a patient's condition have been less than satisfactory for this reason. A further complication arises from the fact that many of these prior art devices are rather bulky, often difficult to use, and generally expensive by present standards.

Various approaches to solving this problem have relied on the measurement of different parameters related to urine discharge in a manner which does not subject the patient to the normal inhibiting environment, as when the voiding must occur in the presence of medical personnel. Such parameters include the maximum flow rate, the force of expulsion, etc. For example, the capability of a patient to rapidly void a large volume of urine generally indicates an absence of a urethral stricture in the patient. If the force of urine discharge is relatively low in spite of a normal voiding volume per unit time, such a condition suggests inadequate contraction of the patient's bladder, rather than a urethral obstruction. This approach is taken by McWhorter in U.S. Pat. No. 4,200,112 which discloses a device for measuring the force of a urine discharge. As disclosed, the device incorporates a plurality of chambers and tubes to define a urine path and utilizes an indicating strip which changes color when wet in order to provide an indication of the maximum height of the liquid reached in one of the urine compartments. Ciarico in U.S. Pat. No. 3,871,231 discloses a device for measuring the approximate peak flow of urine discharge. Like the device disclosed in the McWhorter patent, this device comprises a plurality of chambers and tubes with an indicator strip that changes color when wet.

Profy in U.S. Pat. No. 3,561,427 discloses a device for measuring the volume of urinary output during a given period of time. This device includes a compartmented drum member which is rotatable about a central axis at a predetermined rate or at periodic intervals, driven by an electric motor and a gear mechanism. The drum member has outer wall portions which are transparent and carry suitable graduations for indicating the volume of urine collected in each compartment, thus enabling the average flow rate to be determined.

German Offenlegungsschrift 2,421,746 discloses urine flow rate measuring equipment comprising a measuring cylinder secured in the top of a graduated flexible bag. Part of the flow is diverted into a drip chamber where it can be collected and its volume measured.

U.S. Pat. No. 4,131,016 of Layton also discloses a peak flow rate measuring device which incorporates a collection bag coupled to a primary receiver in which is removably mounted a graduated standpipe. This device provides a discrete indication as to whether the peak flow rate of urine discharge is above or below a predetermined value, which value may be preselected by adjusting the height of the standpipe within the receiving chamber.

All of the devices referred to thus far are more or less complex in construction and require the fabrication and assembly of a number of separate parts in manufacturing the finished device. Some incorporate moving parts which can get out of order or adjustment and therefore present some difficulty in making reliably repeatable measurements.

One particular flowmeter which has found fairly general acceptance by the medical profession for enabling a measurement of the maximum flow rate of urine discharge is disclosed in the Drake, Jr., U.S. Pat. No. 2,648,981. The device disclosed in this patent comprises a liquid conduit having a plurality of calibrated, vertically spaced orifices amd a compartmented receptacle for collecting liquid which is discharged through the respective orifices. As urine (or any liquid) enters the device, the number of compartments which receive liquid through the respective conduits depends upon the rate of flow, since the urine only reaches the second conduit if the rate of discharge exceeds the permissible flow rate through the first conduit, and only reaches the third conduit if the flow rate exceeds the maximum permissible flow through the first and second conduits, etc.

According to Drake, Jr., medical experience has determined that the normal rate at which a patient voids urine is substantially 20 cc. per second and the disclosed flowmeter is designed to detect deviations from this normal rate. The device is designed to provide measurements which are reasonably accurate for increments of 5 cc. per second, which is sufficient for a satisfactory diagnosis to be made by the physician. Even the Drake, Jr. flowmeter, however, is sufficiently expensive to manufacture that it is the common practice of reuse the device repeatedly, after washing, rather than disposing of the device after a single use. Furthermore, the construction of the device is such that it is difficult to obtain a satisfactory urine specimen from the device. Normally, a specimen is desired for analysis along with the measurement of flow rate which is useful for diagnosis. After the patient has used the Drake, Jr. device, however, he is generally unable to provide a separate specimen by further voiding.

None of the devices disclosed in the patents referenced above possesses the capability of providing a measurement record which is suitable for placing in the patient's file, along with other printout records such as EKG charts, automatic blood pressure and pulse rate recordings, and the like. It would be helpful if there were available a urinometer which is simple to produce, simple to use, low enough in cost to be disposable after use, and capable of automatically generating a permanent patient record for retention in the patient's medical file. The urinometer of the present invention is such a device.

SUMMARY OF THE INVENTION

In brief, arrangements in accordance with the present invention utilize the principle of the Drake flowmeter as disclosed in U.S. Pat. No. 2,648,981, the disclosure of which is incorporated herein by reference, in providing a plurality of restricted flow conduits communicating with a urine receiving chamber in a manner such that the height of the urine within the chamber, which is dependent upon flow rate, determines the number of individual conduits which are subject to the flow of urine therethrough. A record member is associated with the urinometer which has the capability of recording the presence of urine at selected points in the urinometer, thereby developing a permanent record that can be detached after the urinometer is used and placed in the patient's file after being utilized in the physician's diagnosis.

One particular arrangement in accordance with the present invention utilizes a variation of the Drake device in which a liquid crystal ink is painted about the outside of the cylindrical member in which the sectored compartments are situated, with a photosensitive record member being removably mounted about the ink-coated surface. This liquid crystal ink is thermally responsive, changing from opaque to translucent at a temperature selected to correspond to the temperature of the human body. Thus, as discharged urine enters a given compartment, its temperature causes the ink on the outside of the compartment wall to "open up", changing its condition from opaque to translucent in the wall area where the urine is present. This permits light to reach the photosensitive record member, causing it to record the presence of urine in adjacent compartments. Graduations are provided on the photosensitive record member so that the amount of urine in the adjacent compartment can be immediately recorded. After use in the conventional manner in which the Drake, Jr. flowmeter is employed, the photosensitive record member can be peeled off the urinometer and its record read for diagnosis, with the record member being retained in the patient's file, if desired.

While the arrangement in accordance with the present invention which has just been described as utilizing a variant of the Drake flowmeter device is sufficiently costly to manufacture as to preclude it from being considered as disposable urinometer, the remaining embodiments of the present invention are adapted to be fabricated in a manner which substantially reduces their cost and renders them readily disposable after a single use. These emodiments of the present invention generally comprise a plastic sheet which is vacuum formed into a predetermined configuration and backed by a thin mylar sheet which completes the formation of the various receptacles, passages and conduits making up the embodiments. In contradistinction to many of the urinometers and flow measuring devices of the prior art, including the Drake device, these embodiments are designed for use over a toilet while the patient is voiding in the normal manner so that urine flowing through the device discharges into the toilet.

One particular arrangement in accordance with the present invention incorporates a plurality of peel-off strips, one of which is a photosensitive record member, mounted along the backside of the mylar sheet on which strips of liquid crystal ink are deposited. The liquid crystal inks respond to the heat from the urine in various conduits on the front side of the mylar sheet, thereby permitting the photosensitive record member to be exposed to light through those liquid crystal ink strips which have changed condition from the presence of the warm urine. After use, the peel-off strips are removed and the photosensitive record member is separated from the other strips by the physician.

In another arrangement in accordance with the invention, liquid crystal ink capsules or tablets of a corresponding meltable dye or ink are employed which melt at body temperature. The melted liquid marking substance runs along small liquid permeable tubes adjacent the conduits in which urine flows through the device. A backing strip of blotter paper or the like absorbs the melted ink and thus provides a permanent record which can be used for diagnosis and placement in the patient's file.

I have also incorporated in one embodiment of the invention an arrangement whereby a suitable midstream urine specimen can be collected automatically, concurrently with the use of the urinometer in the manner described. Thus, although the use of this device discharges urine into the toilet, a selected portion is collected in an associated specimen container, thus avoiding the problem of collecting a urine specimen in addition to developing the desired flow rate measurements.

BRIEF DESCRIPTION OF THE DRAWING

A better understanding of the present invention may be had from a consideration of the following detailed description, taken in conjunction with the accompanying drawings in which:

FIG. 5 is a partial sectional view, taken along the line 5—5 of FIG. 3;

FIG. 6 is a view of a patient record produced from use of the device of FIG. 3;

FIG. 7 is a rear view, partially broken away, of the record of FIG. 6 with protective covering;

FIG. 8 is a front view of a finished device corresponding to FIG. 3;

FIG. 9 is a rear view of the device of FIG. 8;

FIG. 10 is a partial sectional view taken along the line 10—10 of FIG. 9;

FIG. 11 is a front view of a variant of the device of FIG. 3; and

FIG. 12 is a side view of the device of FIG. 11.

DESCRIPTION OF THE PREFERRED EMBODIMENTS

Figure 1:
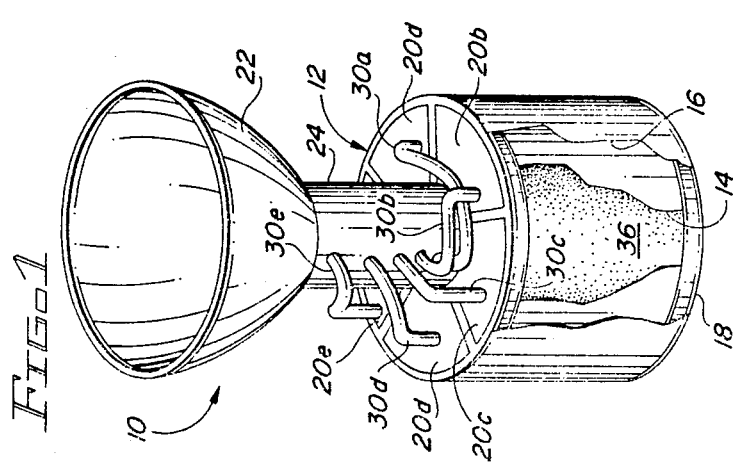
FIG. 1 is a perspective view, partially broken away, of one particular arrangement in accordance with the present invention.

FIG. 1 shows a first embodiment 10 of a uninometer and patient record combination in accordance with the present invention. The device 10 comprises a Drake-type urinometer 12 with a patient record 14 associated therewith in position to develop a record indicating the urinometer measurement. The patient record 14 is covered by a protective cover sheet 16.

As described in the Drake patent, the urinometer 12 comprises a cylinder 18 having a plurality of compartments 20a–20e and a funnel-shaped receiver 22 mounted above the cylinder 18 on a hollow column 24. The column 24 is provided with a central bore (not shown) forming a chamber which communicates with each of a plurality of conduits 30a–30e which extend respectively to direct liquid into compartments 20a–20e. These conduits connect to the column 24 and the internal liquid chamber therein at different levels and are arranged in a generally vertical array, one above the other. As a user voids into the receiver 22, the urine flows downward within the column 24 and begins flowing out the conduit 30a communicating with the bottom of the chamber to be deposited in the compartment 20a initially. If the rate of voiding exceeds th flow rate of the conduit 30a, urine rises to the level of conduit 30b and begins depositing in compartment 20b. If the rate of voiding exceeds the combined flow rates of conduits 30a and 30b, urine rises to the level of 30c and begins depositing in compartment 20c; similarly for conduits 30d, 30e and compartments 20d, 20e. This arrangement is designed so that at a normal rate of voiding of approximately 20 cc. per second, urine will be transferred into compartments 20a, 20b, 20c and 20d, but not compartment 20e. Compartment 20e only receives the urine if the rate of voiding exceeds approximately 25 cc. per second. Correspondingly, if the voiding rate is between approximately 15 and 10 cc. per second, only compartments 20a–20c will receive urine. Thus, the flow rate is determined by monitoring the number of compartments which are left with liquid therein.

The device 10 of FIG. 1 includes a coating 36 of liquid crystal ink painted or otherwise deposited on the exterior surface of the cylinder 18. This liquid crystal ink is of the type well known in the art, which is responsive to temperature so that at a selected temperature level it changes color from a black opaque condition to a light-colored, translucent condition. The liquid crystal ink of the coating 36 is selected to "open up"--i.e., to change from black opaque to a translucent condition--at approximately normal body temperature. Thus, heat from urine at normal body temperature in those compartments 20a–20e to which urine has been directed passes through the thin walls of the cylinder 18 to reach the adjacent portions of the liquid crystal ink coating 36, causing those portions to change condition and become translucent to incident light. Thus, only the portions of the liquid crystal ink coating 36 which are adjacent compartments into which urine has transferred, and then only the portions of the coating 36 opposite those compartments which are coextensive with the level of urine in the respective compartments, become translucent. Ambient light passes through these translucent portions to expose the patient record 14. Thereafter, the patient record 14 and protective cover 16 may be removed from the cylinder 18, with the patient record 14 being analyzed by medical personnel and placed in the patient's file for future reference.

Figure 2:
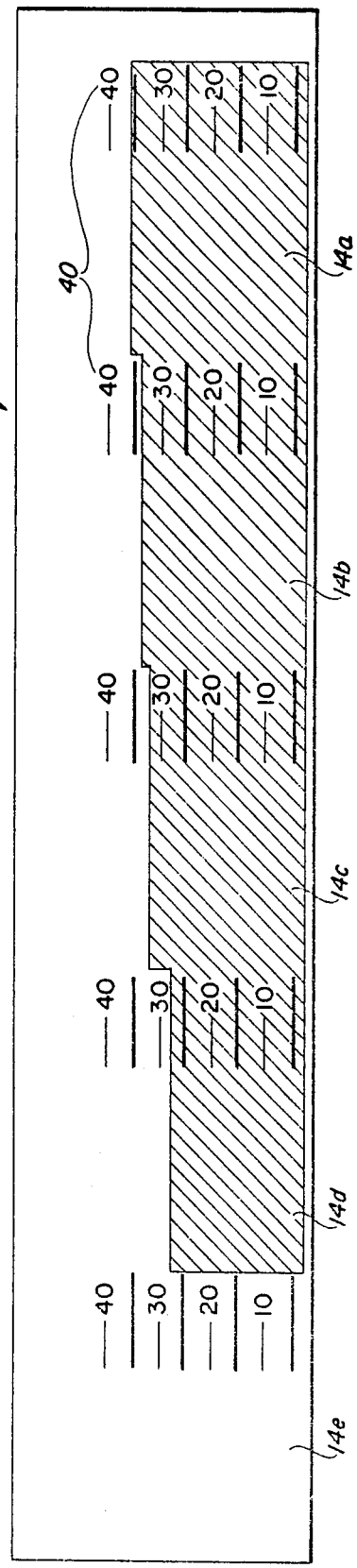
FIG. 2 represents a patient record produced in the use of the device of FIG. 1.

Such a patient record is shown in FIG. 2. In this figure, the record 14 is pre-printed with graduation marks 40 corresponding to the positions of each of five compartments 14a–14e. The shaded areas on the record 14 show portions of the record which have been exposed as a result of the portions of the liquid crystal ink coating 36 opening up due to heat from urine in four compartments of the flowmeter 10. Portions 14a–14d of record 14 are visibly distinguishable from the remainder of the record member, and from the record 14 it can be determined that a total of approximately 125 cc. of urine was voided into the urinometer 10 at a normal rate of approximately 20 cc. per second. If the rate had reached 25 cc. per second, there would be some indication in the section 14e of urine having reached the compartment 20e. If the rate had been less than 20 cc. per second, the portion 14d would not be affected.

Figure 3:
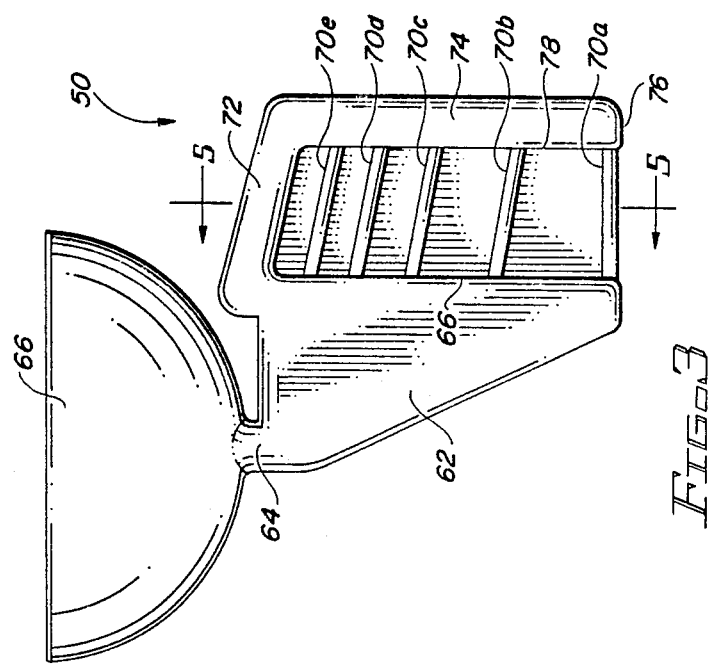
FIG. 3 is a front elevational view of one particular alternative arrangement in accordance with the present invention.

FIG. 3 illustrates an alternative embodiment of the invention and shows a device 50 which is constructed from a thin sheet of transparent plastic which is vacuum formed to the configuration shown. It will be understood that the device 50 will have the general outline illustrated in FIG. 8, for example, which shows untrimmed sheet borders surrounding the formed portion that have been omitted from FIG. 3 for simplicity of presentation.

Figure 4:
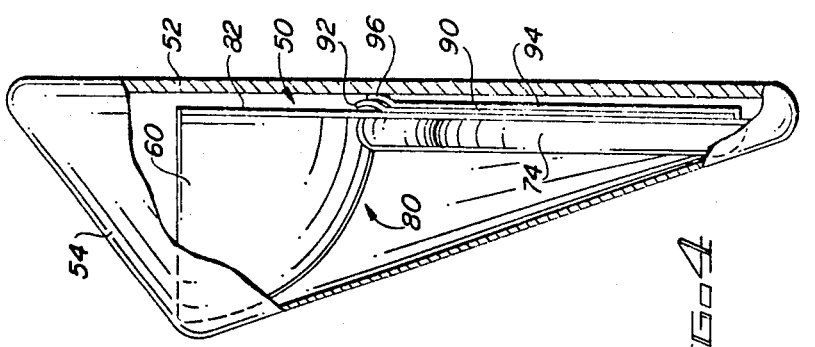
FIG. 4 is a side view, partially broken away, showing the device of FIG. 3 as packaged for distribution.

FIG. 4 is a side view of the device 50 of FIG. 3, shown as it is packaged for distribution on a backing board 52 of cardboard or stiff paper or the like and covered with an opaque covering 54 to protect the device from unwanted exposure to light prior to actual use.

As shown in FIGS. 3 and 4, the device 50 comprises a generally bowl-shaped receiver 60 coupled to a plenum chamber 62 by a necked-down portion or tube 64 at the bottom of the receiver 60. The right-hand side of the plenum 62, as shown in FIG. 3, is a generally vertical sidewall of weir 66 from which a number of small individual conduits 70a, 70b, 70c, 70d, and 70e connect at different levels, one above the other. A larger conduit 72 connects to the upper portion of the plenum 62, extends laterally above the small conduits 70a–70e, and then vertically downward in an outlet tube 74 having an outlet or exit opening 76 for the discharge of urine from the device 50. The outlet tube 74 has a sidewall 78 to which the outlet ends of the small conduits 70a–70e are joined. Thus, any urine entering the plenum 62 will transfer through one or more of the conduits 70a–70e to the outlet tube 74 and will drain through the exit opening 76. The device 50 is intended to be used by a patient standing at a urinal or sitting on a toilet in conventional position.

As is more apparent in the views of FIGS. 4 and 5, the device 50 comprises a vacuum formed front part 80 and a backing sheet 82, preferably of thin transparent plastic film, such as mylar. As shown in the sectional view of FIG. 5, stripes of liquid crystal ink are deposited, as by silk screening, on the back of the thin plastic layer 82 in registration with corresponding conduits of the device 50. Thus, strips 84a–84e are shown in registration with corresponding conduits 70a–70e. A pair of peel-off strips are mounted on the back side of the plastic film sheet 82, covering the liquid crystal ink stripes 84a–84e. These are shown in FIG. 4 as comprising a patient record 90, having a pull tab 92, and a protective covering strip 94 having a pull tab 96. These are shown in further detail in FIGS. 6 and 7.

FIG. 6 illustrates the front side of the patient record strip 90 as developed from the use of the device 50 of FIGS. 3–5. It comprises light responsive stripe portions 91a–91e which were in registration with the liquid crystal ink stripes 84a–84e when the patient record was in position along the back side of the thin plastic film 82, as shown in FIG. 4.. Of these, the stripe portions 91a–91d show the effect of exposure through corresponding liquid crystal ink stripes 84a-84d. In use, the operation of the device 50 and exposure to the patient record member 90 corresponds to the description above with respect to the device 10 in the patient record 14 of FIGS. 1 and 2. The transfer conduits 70a-70e serve to transfer to transfer urine from the plenum 62 to the outlet tube 74, depending on the level of urine in the plenum 62. However, instead of storing urine in separate compartments, the urine is discharged through the exit opening 76 in the bottom of the exit or outlet tube 74 and into the urinal or toilet where the device 50 is used. In flowing through the transfer conduits 70a-70e, the urine at body temperature causes the liquid crystal ink stripes 84a-84e to react and open up to the transmission of light at those conduits transferring urine. Thus, from the resulting patient record 90, the flow rate can be determined. For the record 90 of FIG. 6, with four conduits having transferred urine, a normal flow rate of approximately 20 cc. per second is indicated. Each of the conduits 70a-70e is sized to transfer liquid at approximately 5 cc. per second so that the rate of flow in increments of approximately 5 cc. per second may be indicated.

In the embodiments of the invention where a photosensitive patient record is provided, the photosensitive paper utilized is selected to permit discrimination between the portions of the record which are exposed through the liquid crystal elements and those portions which will become exposed subsequently after the patient record is stripped away from the position adjacent the liquid crystal ink. One way of achieving this discrimination is illustrated in FIG. 7. This shows the patient record 90 and its protective backing sheet 94 with a pattern card 98 in the form of a thin transparent film which is placed between the patient record 90 and the backing sheet 82 bearing the liquid crystal ink stripes 84a-84e. This pattern card 98 is shown having a matrix of intersecting lines 100. Alternatively, the pattern card 98 may bear a pattern of dots or lines or some other suitable pattern which will provide discrimination between those stripe portions such as 91a-91d of the record 90 in FIG. 7 which have been exposed through the liquid crystal ink stripes 84a-84d and the portion 91e that only becomes exposed to light after the photosensitive record 90 is pulled away from the urinometer device 50. It will be understood that the pattern card 98 remains with the backing sheet 82 when the patient record is removed. The photosensitive sheet making up the patient record 90 is prepared so that, upon exposure, it sets permanently within a short period of time, thereby preventing further exposure of the previously exposed stripe portions 91a-91d when the patient record 90 is separated from the device 50.

FIGS. 8 and 9 are respectively front and rear views of a variation of the device 50 shown in FIGS. 3 and 4. In FIGS. 8 and 9, like elements are designated by the same reference numerals, marked with a prime symbol. Thus the device 50' is shown with a receiver 60', a plenum 62', individual transfer conduits 70a'-70e', etc. The device 50' is also shown with a plastic flange 102 which surrounds the aforementioned elements making up the device 50' and represents the portions of the plastic sheet of which the device is formed which are pulled down against the flat portions of the vacuum forming mold. It is these flange portions 102 to which the backing film sheet 82' is adhesively affixed. The rear view in FIG. 9 shows the backing sheet 82' with the portions visible in FIG. 8 being shown in broken line outline. These will normally be visible through the transparent backing sheet 82', and they are shown in broken line outline to provide contrast with the elements which are mounted on the back side of the backing sheet 82'.

The device 50' of FIGS. 8 and 9, instead of relying upon a photosensitive member for the patient record, utilizes blotting paper in conjunction with a substance which melts at body temperature and serves to transfer to the blotting paper.

FIG. 9 shows a plurality of pellets or tablets 110a-110e retained in pockets formed in a vacuum formed plastic film sheet 112. The sheet 112 is shaped to provide a plurality of small channels 114a-114e which communicate with the pockets in which the pellets 110a-110e are placed. The sectional view of FIG. 10 shows the pellet 110b within a pocket 116 adjacent the transfer conduit 70b'. Blotting paper 120 is in place over the pocket 116 and adjacent portions of the sheet 112.

Each pellet 110a-110e may be formed of a particular liquid crystal ink or other suitable material having the property of melting at body temperature and thereafter being absorbed into the adjacent blotting paper to develop a stain or color change thereon. The material of the formed sheet 112 is permeable to the melted substance of the pellets 110a-110e. Thus, as the pellets melt selectively during use of the urinometer 50', the resulting liquid runs along the channels 114a-114e from which it transfers through adjacent portions of the sheet 112 to the adjacent blotting paper. The unit 50' in FIG. 9 is shown in the form in which it is transported, with the packing enclosure removed and prior to preparation for use. The blotting paper strip 116, having a tab 117, is affixed to the backing sheet 82' displaced from the position covering the retainer sheet 112. The reason for this is to avoid marking the blotting paper strip 116 prematurely during transit or storage, as might occur if the unit were subjected to ambient temperatures of 98.6° or higher. When the unit 50' is to be prepared for use, the strip 116 is pulled away from the position on the backing sheet 82' as shown in FIG. 9 and placed directly over the retaining sheet 112. Thereafter, it may be used in the manner described to mark the blotting paper 116 with the melted pellet material, thereby producing a permanent patient record like that shown in FIG. 6.

FIGS. 11 and 12 illustrate a further variation of the vacuum formed embodiment of either FIG. 3 or FIG. 8. Like elements are designated by the same reference numerals with a double prime symbol. Thus the unit 50" is shown with a receiver 60", a plenum 62", plenum wall 66", transfer conduits 70a", 70c", 70d", and 70e", etc. However, in place of the conduit 70b, a conduit 130 is provided which has the same rate of flow as the other transfer conduits but terminates in a flared passage adjacent an opening 132 in the backing sheet 82". The unit 50" differs from the urinometer devices 50 and 50' in that it also includes an arrangement for drawing off a urine specimen from the urine flowing through the transfer conduit 130. A specimen container 134 is shown affixed to the rear side of the backing sheet 82" with its opening in registration with the hole 132 in the backing sheet 82". A collar 136 encircles the neck of the specimen container 134 and is adhesively affixed to the backing sheet 82" through appropriate openings or cutouts in the strips 90", 94". A cap 138 for the container 134 is shown mounted on a plug 140 and affixed to the container 134 by a flexible strand 142. After the urine specimen is collected in the container 134, the container is withdrawn from the urinometer 50", and the cap 138 is taken from the plug 140 and placed on the opening of the neck of the container 134 to seal the mouth of the container.

When the unit 50" is used for the purpose of measuring flow rate and collecting a urine specimen from a patient, the user holds the unit 50 over a toilet and voids into the receiver 60", as previously described. The first portion of urine, which is to be discarded so that a suitable mid-stream sample may be collected in the container 134, flows through the conduit 70a" and out the opening 76". As urine rises in the plenum 62", it begins to flow through the conduit 130. When it reaches the opening 132 communicating with the flared portion of the conduit 130, urine transfers into the specimen container 134 mounted behind the urinometer opposite the opening 132. As the urine specimen enters the bottle 134, air is displaced and flows back out through the opening 132 where it escapes through the outlet tube 74'. When the specimen container 134 is filled, additional urine flowing through the transfer conduit 130 merely flows onward to the outlet tube 74. the unit 50" performs exactly like the unit 50 of FIG. 3 insofar as measurement of flow rate is concerned. However, the unit 50" possesses the capability of also collecting a suitable mid-stream sample of urine at the same time the flow rate is being measured. Neither the collection of the mid-stream urine specimen nor the measuring of voiding rate interferes with the performance of the other function, both being conducted concurrently and effectively.

All of the embodiments of my invention as shown in FIGS. 3–12 are designed to be manufactured so readily and inexpensively as to be clearly disposable after a single use. The patient uses these disposable units in the manner of normal voiding, either at a urinal or sitting on a toilet. All urine, except that which may be retained in the specimen container of FIG. 12, is discharged into the toilet or urinal, thus minimizing the possibility of spillage, mess, etc. Furthermore, it will be appreciated that the Drake type unit of FIG. 1 may be fabricated utilizing the vacuum forming techniques described with respect to FIGS. 3–12 so as to reduce cost and complexity of manufacture, thereby developing another disposable unit.

Both the materials which are used for these disposable units and the methods of fabrication are designed to provide units which can be sold at minimal cost, thereby broadening the user base and rendering them disposable after a single use. Furthermore, arrangements in accordance with my invention advantageously print out a patient record of urine flow rate automatically. This record not only makes for easier, more accurate diagnosis when analyzed by medical personnel, but it also constitutes a record which can be permanently retained in the patient's file for future reference, if desired.

Although there have been described above specific arrangements of a urinometer and patient record combination in accordance with the invention for the purpose of illustrating the manner in which the invention may be used to advantage, it will be appreciated that the invention is not limited thereto. Accordingly, any and all modifications, variations or equivalent arrangements which may occur to those skilled in the art should be considered to be within the scope of the invention as defined in the annexed claims.

What is claimed is:

1. A urinometer combination for developing a patient record during use thereof comprising:
    an input chamber for accepting voided urine;
    a receiving chamber for receiving voided urine transferred from said input chamber;
    a plurality of transfer conduits connecting said input and receiving chambers, each having an inlet coupled to said input chamber at a level different from the levels of the other conduit inlets, and having an outlet in said receiving chamber for transferring urine from said input chamber to said receiving chamber in accordance with the level of urine adjacent said conduit inlets;
    temperature responsive means adjacent said receiving chamber for detecting the presence of urine at a temperature close to body temperature; and
    a record member removably positioned adjacent said temperature responsive means for developing a record corresponding to the condition of said temperature responsive means during use of said urinometer combination.

2. The combination of claim 1 further including a plurality of receptacles individually positioned to receive liquid transferred from the chamber through corresponding transfer conduits, each receptacle being adapted to store therein the liquid which is transferred to it by its corresponding conduit.

3. The combination of claim 2 wherein said receptacles are generally pie shaped in horizontal cross section, being formed by an outer, generally cylindrical wall intersected by a plurality of generally radial partitions, and wherein the temperature responsive means are adjacent the outer surface of the outer wall.

4. The combination of claim 3 wherein the temperature responsive means comprise a layer of thermally responsive ink deposited on said outer wall and extending along the outer surface thereof adjacent all of said receptacles.

5. The combination of claim 4 wherein said thermally responsive ink comprises liquid crystal ink.

6. The combination of claim 4 wherein said record member comprises a strip of material having at least portions thereof which are photosensitive, said strip extending about the generally cylindrical member outside the thermally responsive ink with at least one photosensitive portion for each corresponding receptacle and being adjacent said corresponding receptacle.

7. The combination of claim 6 further including a sheet of opaque material extending about the photosensitive material layer to shield said layer from ambient light, said sheet and said record member being readily removable from the combination and separable from each other to permit separation of the record member for diagnosis and retention in a patient's file.

8. The combination of claim 6 wherein said record member further includes a plurality of graduated markings, corresponding respectively to the relative positions of said receptacles, for enabling measurement of the quantity of liquid in each receptacle in accordance with the record developed on said record member.

9. The combination of claim 1 wherein said input chamber comprises an open topped funnel member, a necked-down passage below said funnel member, and a plenum for collecting urine transferred to said plenum from said funnel member.

10. The combination of claim 9 wherein said receiving chamber comprises an output tube remote from said plenum, each of said transfer conduits having an outlet coupled to said outlet tube.

11. The combination of claim 10 wherein said outlet tube includes an exit opening at the lower end thereof for draining urine from said outlet tube out of said combination.

12. The combination of claim 10 wherein elements constituting said input chamber, receiving chamber, transfer conduits and outlet tube are defined by a vacuum formed sheet of plastic having generally planar portions extending about the peripheries of said elements, and further comprising a generally planar backing sheet adhesively affixed to said planar portions and extending across the back of said elements to complete the same.

13. The combination of claim 12 wherein the temperature responsive means are individually associated with the transfer conduits and are adjacent thereto behind said conduits.

14. The combination of claim 13 wherein the temperature responsive means comprise individual thermally responsive stripes mounted on the rearward surface of said planar sheet, each stripe being generally coextensive with its corresponding transfer conduit.

15. The combination of claim 14 wherein each stripe comprises a thermally responsive ink deposited on the generally planar sheet, and wherein said record member removably mounted along the rear surface of the generally planar sheet in a position encompassing the thermally responsive stripes.

16. The combination of claim 15 wherein said record member comprises photosensitive material in registration with the thermally responsive stripes, and further including a shield member in the form of a strip of opaque material covering the record member.

17. The combination of claim 16 wherein the photosensitive material comprises photosensitive stripes aligned respectively with corresponding thermally responsive stripes.

18. The combination of claim 17 further including a thin transparent sheet having a matrix pattern thereon for enhancing the record developed on the record member during use.

19. The combination of claim 14 wherein the thermally responsive stripes are selected to change condition from opaque to translucent at normal body temperature.

20. The combination of claim 19 wherein the thermally responsive stripes comprise liquid crystal ink painted on the backing sheet.

21. The combination of claim 14 wherein the temperature responsive means comprises individual ink pellets which melt at normal body temperature, and further comprising a formed sheet mounted on the backing sheet behind the transfer conduits, said formed sheet defining a plurality of pockets and corresponding channels communicating with the pockets, each pocket containing one of said pellets.

22. The combination of claim 21 wherein said channels include a rearward portion which is permeable to the liquid ink from said pellets.

23. The combination of claim 22 wherein the record member is adapted to be mounted along the rearward portion of the formed sheet.

24. The combination of claim 23 wherein the record member comprises a strip of blotting paper for developing a record from the liquid ink melted from said pellets during use of the urinometer combination.

25. The combination of claim 12 wherein said backing sheet defines an opening in registration with a selected one of said conduits, and further including a specimen container having a neck portion in registration with said opening for transferring liquid to the container from the selected conduit.

26. The combination of claim 25 wherein said selected conduit is flared adjacent its outlet end for communicating with said opening.

27. The combination of claim 26 further including a collar member surrounding the neck portion of the specimen container for adhesively affixing the specimen container to the backing sheet.

28. The combination of claim 27 wherein the specimen container is removable from the backing sheet and further includes a cap attached to the container by a flexible strand for closing the neck portion opening of the specimen container after removal.

29. The combination of claim 28 wherein the specimen container is a blow-molded bottle having a projecting surface plug for temporarily mounting the cap until the container is ready for sealing.

30. The combination of claim 25 wherein the transfer conduits comprise a first conduit extending between the bottom of the plenum and the bottom of the outlet tube for bypassing the first-voided portion of urine, and wherein the selected conduit is located above the first conduit for transferring to the specimen container a mid-stream portion of voided urine.

31. A combination urinometer and specimen collector device comprising:
   a urinometer comprising a generally planar backing sheet and a vacuum-formed plastic sheet mounted to the front side of the backing sheet, the vacuum-formed sheet defining an input chamber including a plenum, a plurality of individual transfer conduits having their inlet ends coupled to the plenum at different levels one above the other, and an outlet tube coupled to the outlet ends of the individual transfer conduits, said outlet tube having an exit opening at the bottom thereof for draining urine out of the urinometer portion of the device;
   means for developing a detachable patient record during use of the urinometer which is indicative of the rate of voiding in use; and
   a specimen container mounted behind the backing sheet and having a neck portion communicating through an opening in the backing sheet with a selected one of said transfer conduits for collecting a mid-stream portion of voided urine during use of the device.

32. The device of claim 31 further including a first restricted conduit below said selected conduit, the first restricted conduit being effective in preventing initially voided urine from reaching the specimen container.

33. The combination of claim 32 wherein said selected conduit is flared adjacent its outlet end for communicating with said opening.

34. The combination of claim 33 further including a collar member surrounding the neck portion of the specimen container for adhesively affixing the specimen container to the backing sheet.

35. The combination of claim 34 wherein the specimen container is removable from the backing sheet and further includes a cap attached to the container by a flexible strand for closing the neck portion opening of the specimen container after removal.

36. The combination of claim 35 wherein the specimen container is a blow-molded bottle having a projecting surface plug for temporarily mounting the cap until the container is ready for sealing.

* * * * *